US009464934B2

(12) United States Patent
Priore et al.

(10) Patent No.: US 9,464,934 B2
(45) Date of Patent: Oct. 11, 2016

(54) SYSTEM AND METHOD FOR CORRECTING SPECTRAL RESPONSE USING A RADIOMETRIC CORRECTION FILTER

(75) Inventors: Ryan Priore, Wexford, PA (US); John Maier, Pittsburgh, PA (US)

(73) Assignee: Chemimage Technologies LLC, Pittsburgh, PA (US)

(*) Notice: Subject to any disclaimer, the term of this patent is extended or adjusted under 35 U.S.C. 154(b) by 300 days.

(21) Appl. No.: 13/347,788

(22) Filed: Jan. 11, 2012

(65) Prior Publication Data
US 2013/0027701 A1    Jan. 31, 2013

Related U.S. Application Data

(63) Continuation-in-part of application No. 12/931,836, filed on Feb. 11, 2011, now abandoned, and a continuation-in-part of application No. 12/931,868, filed on Feb. 11, 2011, now Pat. No. 8,537,354.

(60) Provisional application No. 61/431,514, filed on Jan. 11, 2011.

(51) Int. Cl.
| | |
|---|---|
| *G01N 21/00* | (2006.01) |
| *G01J 3/02* | (2006.01) |
| *G01J 3/44* | (2006.01) |
| *G01N 21/27* | (2006.01) |
| *G01N 21/65* | (2006.01) |

(Continued)

(52) U.S. Cl.
CPC .............. *G01J 3/02* (2013.01); *G01J 3/0297* (2013.01); *G01J 3/28* (2013.01); *G01J 3/44* (2013.01); *G01N 21/276* (2013.01); *G01N 21/65* (2013.01); *G01J 2003/1213* (2013.01); *G01N 2201/1293* (2013.01)

(58) Field of Classification Search
CPC . H01J 37/32935; G01N 21/64; G01N 21/68; G01N 2015/1037; G01J 3/02
USPC ...................................... 356/72–73
See application file for complete search history.

(56) References Cited

U.S. PATENT DOCUMENTS

| 4,041,308 A | * | 8/1977 | Fujita ..................... G03B 17/12 |
| | | | 250/214 P |
| 5,113,275 A | | 5/1992 | Patel |

(Continued)

OTHER PUBLICATIONS

May, Willie E. et al, National Institute of Standards & Technology, Certificate of Analysis, Standard Reference material, Relative Intensity Correction Standard for Raman Spectroscopy, 532 nm excitation, certificate issue dated Jan. 28, 2004, pp. 1-6.

(Continued)

*Primary Examiner* — Abdullahi Nur
(74) *Attorney, Agent, or Firm* — Pepper Hamilton LLP (57) ABSTRACT

The present disclosure provides for a correction filter that may be configured to comprise a predetermined arrangement of thin film layers. This arrangement of thin film layers may be such that it effectively enables a correction filter to generate a predetermined spectral response, wherein said predetermined spectral response is substantially the same as a determined instrument response correction associated with an instrument. The invention of the present disclosure therefore provides for effectively compensating for transmission inefficiencies associated with an instrument without the need for separate reference measurements to determine and correct for instrument response.

17 Claims, 6 Drawing Sheets

(51) Int. Cl.
*G01J 3/28* (2006.01)
*G01J 3/12* (2006.01)

(56) References Cited

U.S. PATENT DOCUMENTS

| | | | |
|---|---|---|---|
| 5,247,378 A | 9/1993 | Miller | |
| 5,528,295 A * | 6/1996 | Wagner | G01J 3/26 |
| | | | 250/226 |
| 5,568,286 A | 10/1996 | Riza | |
| 5,850,623 A | 12/1998 | Carman | |
| 5,966,240 A * | 10/1999 | Lange et al. | 359/583 |
| 6,353,656 B1 | 3/2002 | LeVert | |
| 6,403,947 B1 | 6/2002 | Hoyt | |
| 6,765,668 B2 | 7/2004 | Gardner | |
| 6,801,310 B2 | 10/2004 | Kewitsch | |
| 7,595,873 B1 | 9/2009 | Deck | |
| 7,901,870 B1 * | 3/2011 | Wach | G02B 5/285 |
| | | | 430/321 |
| 8,610,442 B2 * | 12/2013 | Stevenson et al. | 324/681 |
| 2007/0216898 A1 | 9/2007 | Gardner | |
| 2008/0034833 A1 * | 2/2008 | Maier | 73/1.01 |
| 2008/0062353 A1 | 3/2008 | Wang | |
| 2008/0095467 A1 * | 4/2008 | Olszak et al. | 382/284 |

OTHER PUBLICATIONS

Choquette, Steve, 2009 USP Annual Scientific Meeting, "Spectral Identification," Sep. 22, 2009.

Choquette, S.J, "Standard Reference Materials for Relative Intensity Correction of Raman Spectrometers," American Laboratory, abstract.

International Search Report, PCT/US2007/019688, Sep. 10, 2007.

* cited by examiner

510 determining an instrument response correction associated with an instrument; and

520 designing a correction filter to thereby produce a predetermined spectral response, wherein said predetermined spectral response is substantially the same as said instrument response correction.

610 passing a plurality of interacted photons generated by a sample through a first filter, wherein said first filter is configured so as to effectively compensate for transmission inefficiencies associated with an instrument;

620 collecting at least one plurality of interacted photons generated by a sample using at least one collection optics associated with an instrument

630 detecting said plurality of interacted photons to thereby generate at least one spectroscopic data set representative of said sample.

Figure 6

SYSTEM AND METHOD FOR CORRECTING SPECTRAL RESPONSE USING A RADIOMETRIC CORRECTION FILTER

RELATED APPLICATIONS

This Application is a Continuation-in-Part to the following pending U.S. Patent Applications: U.S. Publication No. US2011/0208462, filed on Feb. 11, 2011, entitled "System and Method for Instrument Correction Using Transmission Efficiency," and U.S. Publication No US2011/0211763, filed on Feb. 11, 2011, entitled "System and Method for Instrument Response Correction Based on Independent Measurement of the Sample." This Application also claims priority under 35 USC §119(e) to U.S. Provisional Patent Application No. 61/431,514, filed on Jan. 11, 2011, entitled "Radiometric Spectral Response Correction filer." Each of the above-reference patent applications is hereby incorporated by reference in its entirety.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array ("FPA") detectors are typically employed. The choice of FPA detector is governed by the spectroscopic technique employed to characterize the sample of interest. For example, silicon ("Si") charge-coupled device ("CCD") detectors or CMOS detectors are typically employed with visible wavelength fluorescence and Raman spectroscopic imaging systems, while indium gallium arsenide ("InGaAs") FPA detectors are typically employed with near-infrared spectroscopic imaging systems.

Wide-field spectroscopic imaging of a sample can be implemented by collecting spectra over the entire area encompassing the sample simultaneously using an electronically tunable optical imaging filter such as an acousto-optic tunable filter ("AOTF") or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet ("UV"), visible ("VIS"), near infrared ("NIR"), shortwave infrared ("SWIR"), mid infrared ("MIR") wavelengths, long wave infrared wavelengths ("LWIR"), and to some overlapping ranges. These correspond to wavelengths of approximately 180-380 nm ("UV"), 380-700 nm ("VIS"). 700-2500 nm ("NIR"), 850-1800 nm ("SWIR"), 650-1100 nm ("MWIR"), 400-1100 ("VIS-NIR") and 1200-2450 ("LWIR").

During spectral analysis, data is subjected to various optical artifacts. For example, putting any component in the path of light may disrupt the efficiency of detection. As a result, the data needs to be corrected to remove these effects because when efficiency of an instrument is affected, any data generated will similarly be affected.

In the case of Raman imaging data the real physical phenomenon being measured is the Raman scattered light emanating from a location in a field-of-view represented by a pixel in a data set. The Raman scattered light passes through a set of imaging optics to a detector. In general the optics are fixed components made of solid materials with stable optical characteristics. In full field-of-view Raman imaging of tissues, one of the optics is a liquid crystal tunable filter spectroscopic imaging element. This is a dynamically tunable narrow bandpass (~0.25 nm FWHM) filter that allows imaging of the same field-of-view at different wavelengths, without moving any optics. The specific advantages an approach based on this hardware are realized in the speed of acquisition and the alignment of images at different wavelengths. A disadvantage of this device is that there can be fluctuations in the transmission efficiency that depend on characteristics such as temperature, atmospheric pressure and humidity. These fluctuations are significantly larger than fluctuations of properties of standard physical optics in the same conditions and manifest themselves in the amount of light that is transmitted, and hence on the amount of Raman scattered light that is recorded at the detector. Because these fluctuations vary with environmental conditions, they manifest themselves differently at different operating conditions.

Due to these fluctuations, an optical instrument operating in a real-life scenario does not have a perfect or ideal performance for all wavelengths of light. This is true at an optical component level, at an optical system level, or both.

Currently, the state of the art relies on separate measurements of a known material to correct for optical artifacts via software correction. There exists a need for a more rapid system and method that allows for real-time instrument response correction. It would be advantageous if a system and method could provide for instrument response correction without requiring a separate measurement, thereby increasing speed of instrument operation and data generation.

SUMMARY OF THE INVENTION

The present disclosure relates to a system and method for correcting instrument response comprising the use of a specialized correction filter. More specifically, the present disclosure relates to a thin film correction filter with a specific associated spectral response. This thin film filter may comprise an interference filter. This correction filter may be configured using a predetermined thin film configuration so the filter generates a specific spectral response substantially the same as a predetermined instrument response correction and may be customized for a plurality of instruments.

The custom designed filter element has a specific spectral response chosen to correct for all instrumental spectral artifacts due to other optical components including but not limited to: light source, tunable filter, optical elements, camera response, and combinations thereof. In one embodiment, each filter comprises uniquely configured thin film components. In one embodiment, the filter element described achieves real time instrument response correction by eliminating the need for separate reference measurements on known standards, such as a NIST standard reference material ("SRM").

The present embodiments provide at least three advantages over the prior art. First, there are no spatial limitations associated with the filter described herein. Second, utilizing the filter described herein eliminates the need to separately collect correction data. This is because the data is, in a sense, already "corrected" by using the filter to collect it. Third, use of the filter is more practical than the prior art because it eliminates the need to use a standard. The correction filter described herein holds potential for application in a variety of instruments for various types of detection.

DETAILED DESCRIPTION

Reference will now be made in detail to the preferred embodiments of the present disclosure, examples of which are illustrated in the accompanying drawings. Wherever possible, the same reference numbers will be used throughout the drawings to refer to the same or like parts.

The present disclosure provides for a system and method which hold potential for enabling the evaluation of an imperfect optical component or system in terms of its transmission or detection performance. In the case where the component or system is stable, the present disclosure contemplates that any deviations from the perfect or ideal performance may be measured and accounted for.

If a spectrum of this source were taken with an ideal instrument, the spectrum would be a flat horizontal line as a function of wavelength. In one embodiment, an ideal light source that produces the same number of photons at each wavelength may be used. When this ideal source is used with an imperfect instrument, however, the measured spectrum is not a straight line. The real spectrum obtained from a perfect source with the same number of photons at each wavelength carries information about the instrument response of the real-world, imperfect optical instrument. The instrument response is the spectral response. In general, instrument response as a function of any number of parameters can be measured and corrected for.

In working with optical systems, the presence of the instrument response—i.e., a manifestation of an instrument's imperfections or deviations from the ideal response—is evident in both dispersive and imaging spectroscopy experiments. For example, in case of a dispersive spectroscopy measurement (e.g., measurement of a Raman spectrum) on a sample with some background fluorescence, it is observed that the baseline on which the Raman spectrum sits is not a flat line. The features in the baseline (e.g., its lack of ideal flatness) have a characteristic that is due in part to the optical components and detectors that comprise the system used for the measurement.

Figure 1:
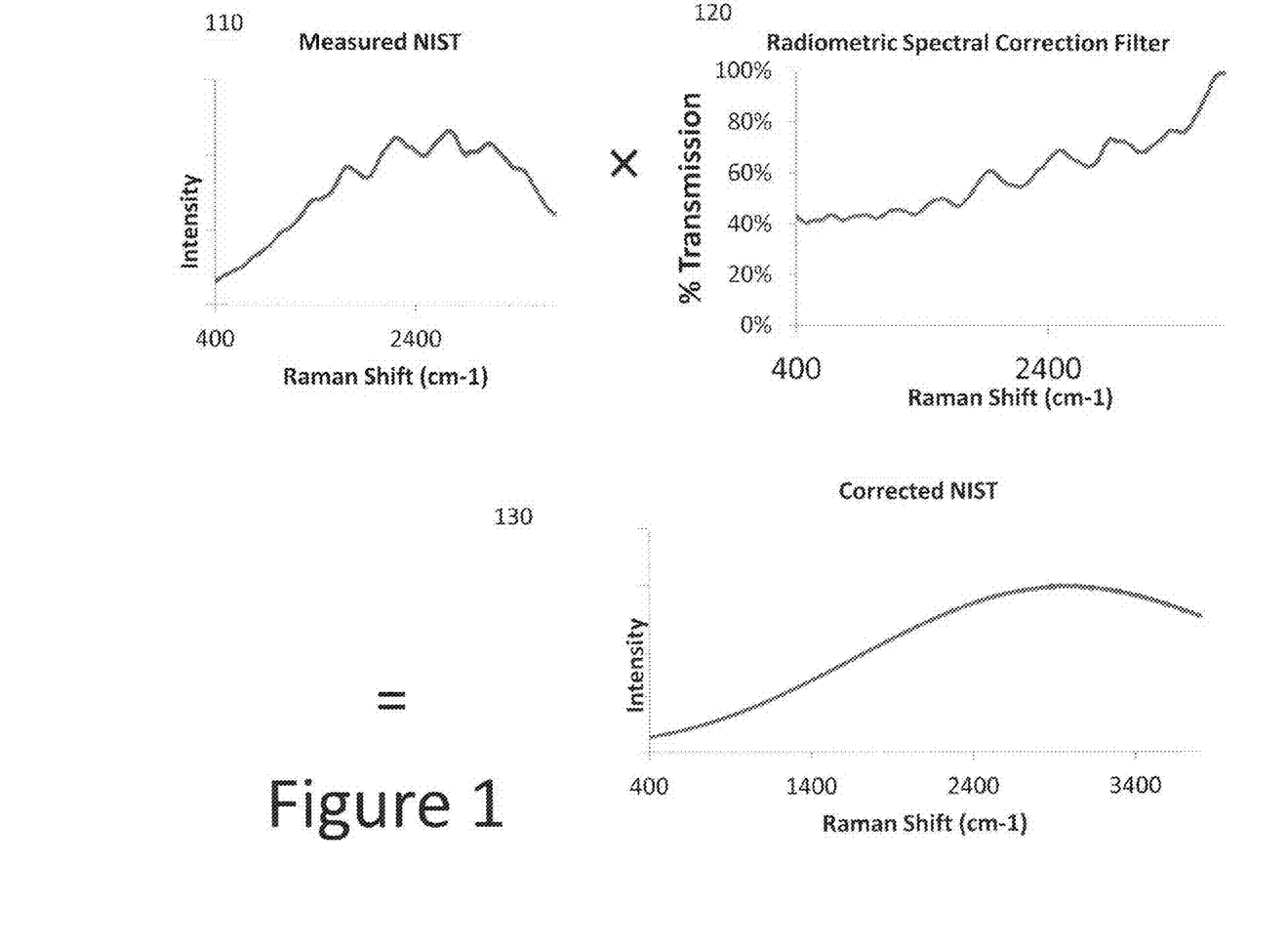
FIG. 1A is illustrative of the wavelength to wavelength variation in transmission of a tunable filter.
FIG. 1B is illustrative of the variance that occurs in filter transmission over time.
FIG. 1C is illustrative of instrument response correction using a NIST standard.

Variations in the transmission of a tunable filter can be demonstrated in a simple experiment by measuring the Raman scattering from a standard material through a liquid crystal tunable filter. The National Institute for Standards and Technology ("NIST") provides a standard reference material (SRM 2242) that has a well characterized spectral response to laser excitation. FIGS. 1A and 1B show a plot of this response with the mean intensity of an image of a piece of this material as a function of Raman shift acquired with a tunable filter-based system. FIG. 1A is illustrative of the wavelength to wavelength variation in the transmission of the tunable filter with the known spectrum of the material (dashed line). A single frame of the image stack is shown to indicate the level of pixel to pixel to noise. FIG. 1B is illustrative of the detailed spectrum of the same measurement made on the same sample at a different time to indicate the variance that occurs in the filter transmission over time. FIG. 1C is illustrative of instrument response correction using a NIST standard.

The Raman image is acquired over the full Raman scattering spectral range. The image is comprised of a series of 196 frames acquired at different center bandpass settings of the filter. The plot represented in the dashed line is the known spectrum of the material provided by NIST. The solid line is the intensity of each frame versus center band setpoint. Along with the plot of mean intensity is shown the mean plus and minus the standard deviation of each frame (dotted lines). This is included to point out that the variance from frame to frame is not due to the pixel noise of the image (which is indicated by the standard deviations).

The transmission spectrum is not smooth; it has sharp discontinuities and could not be well approximated by an analytic equation. The fundamental reason why these discontinuities exist is related to the operation of liquid crystal tunable filters as a collection of independently functioning liquid crystal elements stacked together.

The tunable filter works by aligning the center bandpass of a series of liquid crystal elements which can each be independently adjusted in terms of a periodic (as a function of wavelength) transmission function. The overall bandpass of the filter is determined by the multiplication of the transmission of each of the elements. In order to select a specific center bandpass for the whole filter, an operating point is chosen for each element of the filter. During the manufacturing process the filter performance is optimized around high center bandpass throughput and high out-of-band light rejection. In order to perform this optimization, operating point choices are made that can lead to very different operating points for a given element at two adjacent wavelength setpoints. Because the choices of operating points are driven by out-of-band rejection, transmission smoothness is sacrificed. This is true about filters from multiple vendors with different designs.

If the transmission function were constant, a simple ratiometric correction would be feasible. Data from a measurement identical to that shown in FIGS. 1A and 1B on the same instrument and sample illustrates how this discontinuous transmission curve changes over time. FIG. 1B illustrates the mean and standard deviation spectra for a second measurement on the same instrument. The assumption here is that of all of the components in the system, the tunable filter is the least stable in terms of behavior over time. This assumption is supported by the clear presence of discontinuities consistent with filter reset points in the spectra shown and the fact that all of the other fixed optics in the system have smooth transmission functions over the relevant wavelength range.

An instrument response correction ("IRC") relates a set of measurable physical properties (the truth) to the output of an instrument (the measurement). In the case of the measurement of Raman scattered light at any wavelength, λ, there is a simple relationship between the measured intensity and the actual number of photons that are emanating from a sample:

$$R(\lambda)_{Meas} = \alpha(\lambda)_{IRC} \times R(\lambda)_{true}.$$

In this case $\alpha_{IRC}$ is a unitless scalar that is essentially the transmission efficiency of the system at the wavelength being studied. Actual measurements are made in the units of output of the CCD camera. For the purposes of the relationship above, the unit conversions are ignored because they do not impact the instrument response correction and $R_{Meas}$ and $R_{true}$ should be considered to include such unit conversions that are necessary to move them both into the unit of detector counts.

Figure 2A:
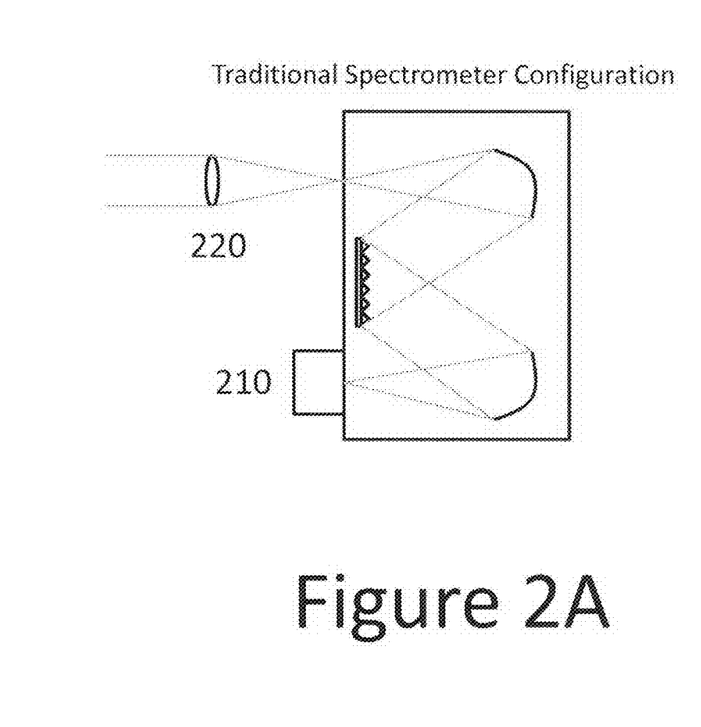
FIG. 2A is an exemplary schematic of a traditional spectrometer configuration.
Figure 2B:
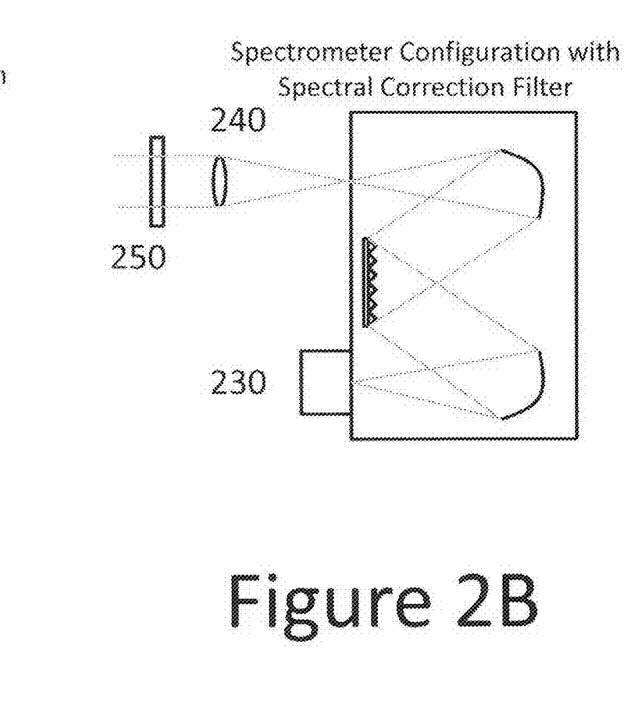
FIG. 2B is an exemplary schematic of a spectrometer configuration using a spectral correction filter.

The present disclosure provides for a system and method for achieving real-time instrument response correction. A customizable correction filter holds potential for correcting or leveling the optical artifacts present in a spectrometer based instrument. This physical "leveling" correction filter holds potential for enabling real-time correction of optical artifacts at a hardware level. In one embodiment, every spectrometer-based instrument may comprise an associated unique correction filter. In one embodiment, a correction filter may comprise a spectral radiometric correction filter. FIG. 2A illustrates a traditional spectrometer configuration. FIG. 2B is an exemplary schematic of a spectrometer configuration using a spectral correction filter. In one embodiment, illustrated by FIG. 2A, a traditional spectrometer configuration may comprise a collection optics 220 and a detector 210. In the spectrometer configuration of FIG. 2B, which illustrates an embodiment comprising a spectral correction filter may comprise a collection optics 240, a detector 230, and a correction filter 250, in addition to other elements those skilled in the art will recognize are necessary for the proper operation of the instrument. In FIG. 2B, the correction filter 250 is illustrated as being placed before a collection optics 240, however, the present disclosure contemplates that this correction filter may be place at any location in an instrument where the light passing through the instrument will be collimated, the light is orthogonal to the correction filter.

Figure 3:
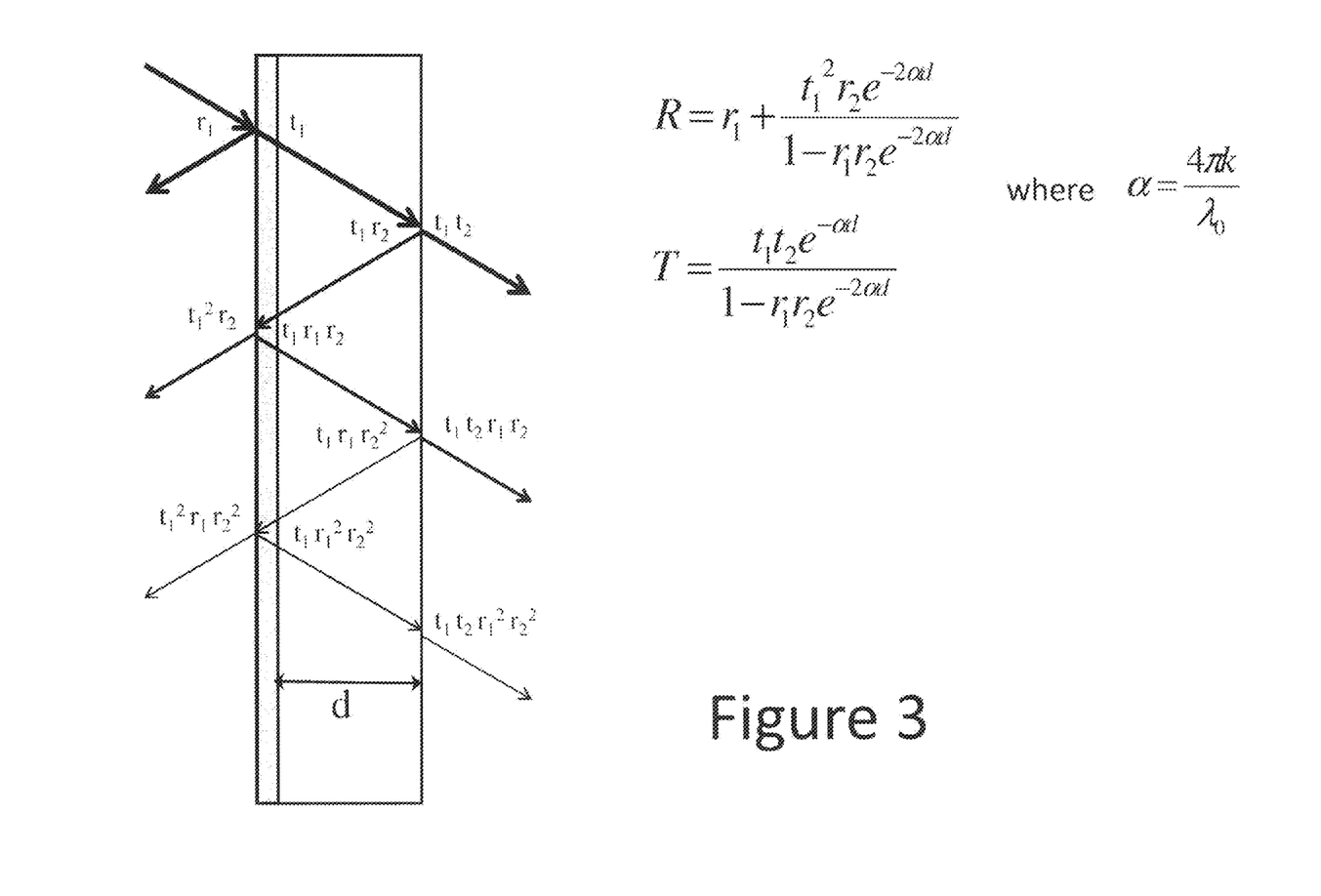
FIG. 3 is illustrative of the capabilities of the present disclosure for determining a instrument response.
Figure 4:
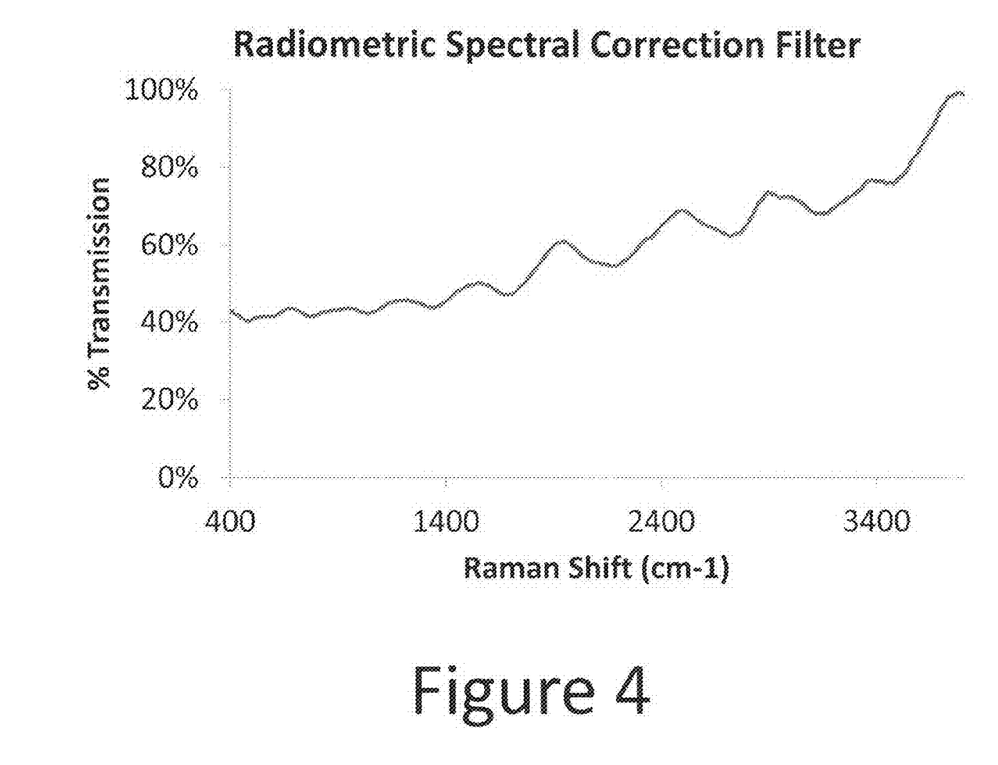
FIG. 4 is representative of transmission efficiency by wavelength of a spectral correction filter of the present disclosure.

FIG. 3 is illustrative of the capabilities of determining an instrument response. FIG. 4 is illustrative of the use of a radiometric correction filter as contemplated by the present disclosure.

The present disclosure contemplates that thin film optics may hold potential as a method of producing such filters. The present disclosure provides for a correction filter comprising a substrate and a plurality of thin film layers arranged in a predetermined configuration so as to enable said filter to generate a predetermined spectral response, wherein said predetermined spectral response is substantially the same as a determined instrument response correction associated with an instrument. This arrangement may be such that it acts to effectively compensate for transmission inefficiencies associated with an instrument. In one embodiment, these thin film components may be arranged in a predetermined configuration. In one embodiment, a substrate may comprise at least one of: quartz, silica, N-BK7 and combinations thereof.

Thin film components may include those comprising materials associated with a high refractive index such as niobium pentoxide ($Nb_2O_5$), titanium dioxide ($TiO_2$), silicon (Si), germanium (Ge), and combinations thereof. Thin film components may also comprise materials associated with a low refractive index, such as magnesium fluoride ($MgF_2$), aluminum oxide ($Al_2O_3$), silica ($SiO_2$), and combinations thereof. Thin film components may also comprise a combination of materials associated with a high refractive index and materials associated with a low refractive index.

To determine an appropriate thin film component configuration, an optimization process may be implemented. During this optimization process, various different thin film configurations may be assessed until a configuration is achieved that adequately corrects for instrument response of a particular instrument. For example, changing the thickness of these thin film components may result in changes in the dramatic features of associated spectra generated. This thin film configuration may be implemented in a correction filter which can be associated with an instrument. This correction filter, now part of the instrument, effectively applies an instrument response correction to data generated using the instrument, eliminating the need for separate correction measurements.

In one embodiment, the transmission spectrum of the custom designed filter element is the inverse of the measured spectral response for each instrument. This allows for the matching of the percent transmission of the thin film components to the percent transmission of the instrument response. The filter holds potential for addressing a broad range of spectrometer based instrumentation.

This filter element can be incorporated into a multi-conjugate filter ("MCF"), a system with an MCF, or a system with at least one of: a tunable filter, an interferometer, a fiber array spectral translator device ("FAST device"), a dispersive spectrometer, and combinations thereof. MCF technology is available from ChemImage Corporation, Pittsburgh, Pa., and more fully described in the following U.S. Patents and Published U.S. Patent Applications: U.S. Pat. No. 7,362,489, filed on Apr. 22, 2005, entitled "Multi-Conjugate Liquid Crystal Tunable Filter," U.S. Pat. No. 6,992,809, filed Feb. 2, 2005, also entitled "Multi-Conjugate Liquid Crystal Tunable Filter," and U.S. Publication No. US 2011-0279744, filed on Apr. 14, 2011, entitled "Short wave infrared multi-conjugate liquid crystal tunable filter." Each of these patents and patent applications are hereby incorporated by reference in their entireties.

A FAST device may comprise a two-dimensional array of optical fibers drawn into a one-dimensional fiber stack so as to effectively convert a two-dimensional field of view into a curvilinear field of view, and wherein said two-dimensional array of optical fibers is configured to receive said photons and transfer said photons out of said fiber array spectral translator device and to at least one of: a spectrometer, a filter, a detector, and combinations thereof. In one embodiment, a system of the present disclosure may comprise FAST technology available from ChemImage Corporation, Pittsburgh, Pa. This technology is more fully described in the following U.S. Patents, hereby incorporated by reference in their entireties: U.S. Pat. No. 7,764,371, filed on Feb. 15, 2007, entitled "System And Method For Super Resolution Of A Sample In A Fiber Array Spectral Translator System"; U.S. Pat. No. 7,440,096, filed on Mar. 3, 2006, entitled "Method And Apparatus For Compact Spectrometer For Fiber Array Spectral Translator"; U.S. Pat. No. 7,474,395, filed on Feb. 13, 2007, entitled "System And Method For Image Reconstruction In A Fiber Array Spectral Translator System"; and U.S. Pat. No. 7,480,033, filed on Feb. 9, 2006, entitled "System And Method For The Deposition, Detection And Identification Of Threat Agents Using A Fiber Array Spectral Translator".

The correction filter disclosed herein holds potential for application in a variety spectroscopic modalities including Raman, fluorescence, visible, ultraviolet, and infrared including short wave infrared, near infrared, mid infrared, long wave infrared, and combinations thereof.

Instrumentation exploiting absorbance phenomena will utilize a "white" "flat" sample. For example, the filter of the present disclosure can be implemented in infrared spectroscopy, including but not limited to near infrared (NIR) and short wave infrared (SWIR). Currently, infrared spectroscopy utilizes a two-step process. First, the sample data is collected. Then, data is collected form a reflectance standard (a "white", "flat" sample). The data sets are divided to achieve the absorbance data. This disclosure contemplates an embodiment of the correction filter disclosed herein that eliminates the need for the division step of the data collection process.

In another embodiment, the filter disclosed herein eliminates the need to collect multiple reference data sets. In such an embodiment, one reference data set can be collected and repeated for N number of reference data sets. Because the transmission spectrum of the custom designed filter element is the inverse of the measured spectral response for each instrument, the spectral response of a system with such a filter integrated would be "flat" (e.g. the spectrum of a white sample will be featureless for absorbance instrumentation). This component allows measurements to be performed without the use of a reference measurement.

Figure 5:
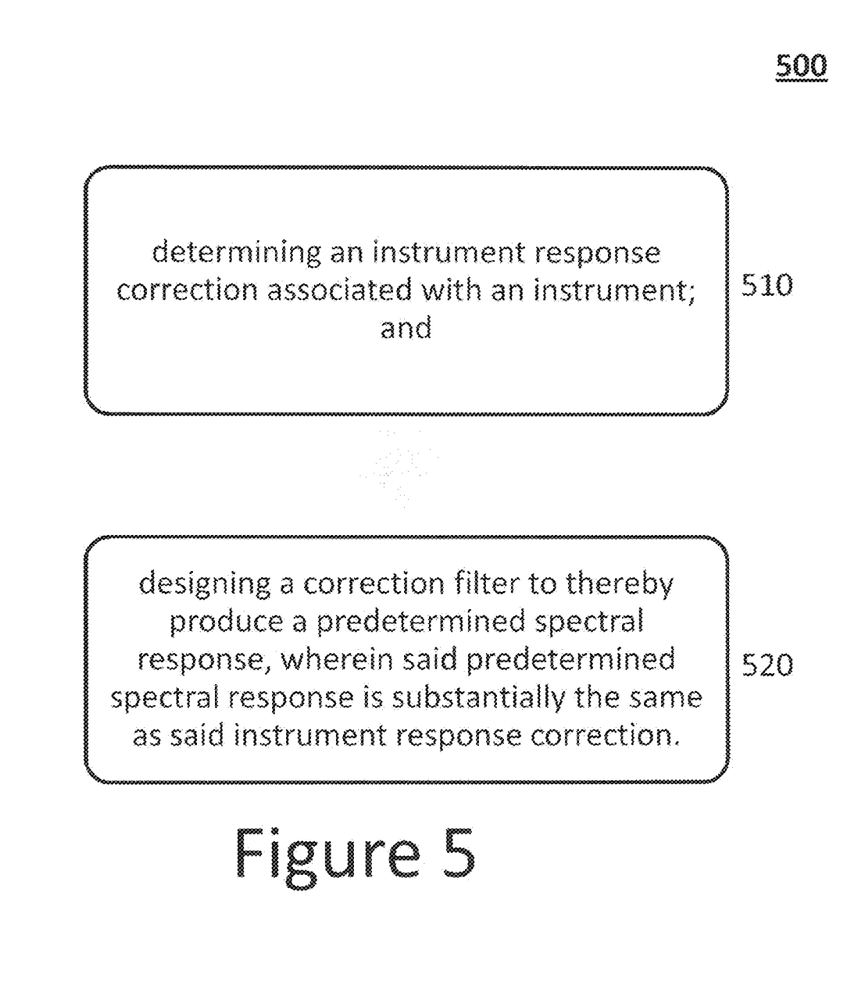
FIG. 5 is representative of a method of the present disclosure.

The present disclosure also provides for a method for correcting transmission inefficiency of an instrument. One embodiment, illustrated by FIG. 5, a method 500 may comprise determining an instrument response correction associated with an instrument in step 510. In step 520, a correction filter may be designed to thereby produce a predetermined spectral response, wherein said predetermined spectral response is substantially the same as said instrument response correction. In one embodiment, a said predetermined spectral response is such that it effectively compensates for transmission inefficiencies associated with said instrument. In one embodiment, a correction filter further comprises a thin film interference filter, comprising a plurality of thin film layers arranged in a predetermined configuration. As discussed herein, a thin film configuration is further determined by performing an optimization process.

Figure 6:
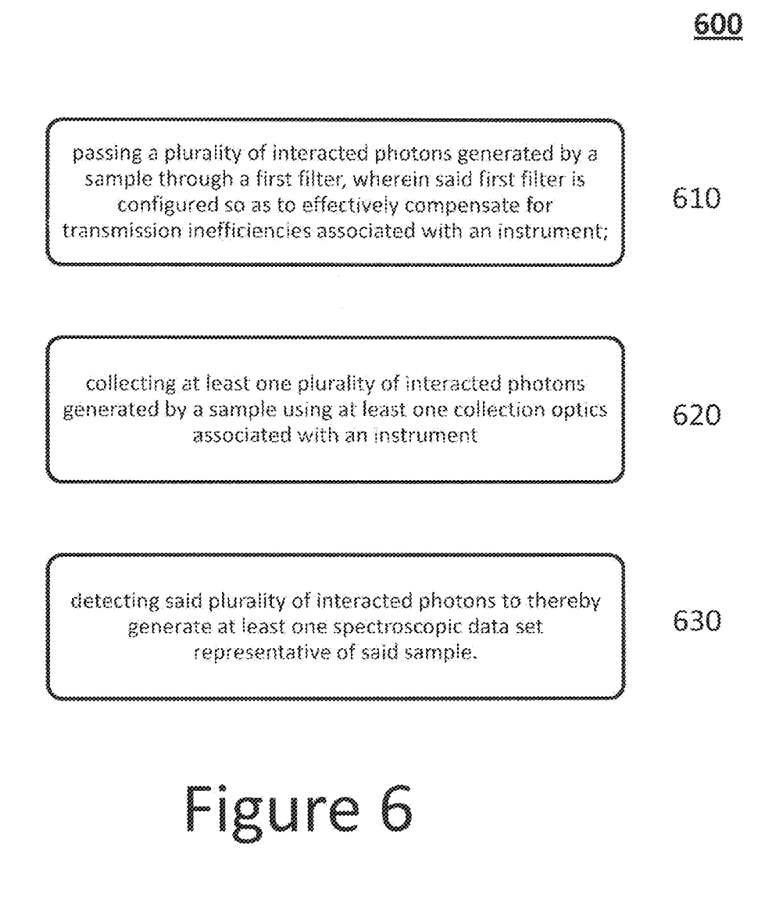
FIG. 6 is representative of a method of the present disclosure.

The present disclosure also provides for a method, illustrated in FIG. 6. In such an embodiment, the method 600 may comprise collecting at least one plurality of interacted photons generated by a sample using at least one collection optics associated with an instrument in step 610. In step 620, a plurality of interacted photons may be passed through a first filter, wherein said first filter is configured so as to effectively compensate for transmission inefficiencies associated with said instrument. In step 630, a plurality of interacted photons may be detected to thereby generate at least one spectroscopic data set representative of said sample. In one embodiment, compensation for transmission inefficiencies may be achieved by further configuring at least one thin film element associated with said first filter to thereby generate a predetermined spectral response, wherein said predetermined spectral response is substantially the same as an instrument response correction associated with said instrument.

In one embodiment, the method 600 may further comprise passing said plurality of interacted photons through a at least one of: a second filter, an interferometer, a dispersive spectrometer, a fiber array spectral translator device, and combinations thereof. In one embodiment comprising a second filter, said second filter may be configured so as to sequentially filter said plurality of interacted photons into a plurality of predetermined wavelength bands. In one embodiment a second filter further comprises a filter selected from the group consisting of: a liquid crystal tunable filter, a multi-conjugate tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof.

In one embodiment, an interferometer may be selected from the group consisting of: a polarization-independent imaging interferometer, a Michelson interferometer, a Sagnac interferometer, a Twynam-Green interferometer, a Mach-Zehnder interferometer, and a tunable Fabry Perot interferometer, and combinations thereof.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A method for correcting transmission inefficiency of an instrument, the method comprising:
    generating an optical response from a spectrometer-based instrument;
    comparing the optical response to a predetermined spectral response for the instrument;
    calculating a transmission inefficiency between the optical response and the predetermined spectral response; and
    correcting the transmission inefficiency of the optical response by inserting into the instrument a correction filter including a thin film interference filter having a plurality of thin film layers arranged in a predetermined configuration.

2. The method of claim 1, further comprising optimizing the thin film configuration to correct the transmission inefficiency between the optical response and the predetermined spectral response.

3. A correction filter comprising:
    a substrate; and
    a plurality of thin film layers arranged in a predetermined configuration on the substrate, wherein the plurality of thin film layers is configured to correct a transmission inefficiency in an optical response to substantially a predetermined spectral response of an instrument.

4. The correction filter of claim 3, wherein the plurality of thin film layers comprises one or more of a thin film layer comprising a high refractive index material and a thin film layer comprising a low refractive index material.

5. The correction filter of claim 3, wherein the substrate further comprises one or more of quartz, silica, and N-BK7.

6. The correction filter of claim 3, wherein the plurality of thin layer films comprise one or more of niobium pentoxide ($Nb_2O_5$), titanium dioxide ($TiO_2$), silicon (Si), and germanium (Ge).

7. The correction filter of claim 3, wherein the plurality of thin layer films comprise one or more of magnesium fluoride ($MgF_2$), aluminum oxide ($Al_2O_3$), and silica ($SiO_2$).

8. A method comprising:
    passing a plurality of interacted photons through a first filter comprising a thin film interference filter having a plurality of thin film layers arranged in a predetermined configuration, the first filter being configured to correct an optical signal of an instrument to substantially a predetermined spectral response;
    collecting at least one plurality of interacted photons generated by a sample using at least one collection optic associated with the instrument; and
    detecting the plurality of interacted photons to generate at least one spectroscopic data set.

9. The method of claim 8, further comprising passing the plurality of interacted photons through one or more of a second filter, an interferometer, and a dispersive spectrometer.

10. The method of claim 8, further comprising a second filter configured to sequentially filter the plurality of interacted photons into a plurality of predetermined wavelength bands.

11. The method of claim 10, wherein the second filter comprises one or more of a liquid crystal tunable filter, a multi-conjugate tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, and a Fabry Perot liquid crystal tunable filter.

12. The method of claim 8, further comprising an interferometer selected from the group consisting of a polarization-independent imaging interferometer, a Michelson interferometer, a Sagnac interferometer, a Twynam-Green interferometer, a Mach-Zehnder interferometer, and a tunable Fabry Perot interferometer.

13. An instrument comprising:
    at least one collection optic configured to collect at least one plurality of interacted photons generated by a sample;
    a first filter comprising a thin film interference filter having a plurality of thin film layers arranged in a predetermined configuration, the first filter being configured to correct an optical signal of the instrument to substantially a predetermined spectral response for the instrument; and
    at least one detector configured to detect the plurality of interacted photons and generate at least one spectroscopic data set.

14. The instrument of claim 13, further comprising one or more of a second filter, an interferometer, and a dispersive spectrometer.

15. The instrument of claim 13, further comprising a second filter configured to sequentially filter the plurality of interacted photons into a plurality of predetermined wavelength bands.

16. The instrument of claim 15, wherein the second filter comprises one or more of a liquid crystal tunable filter, a multi-conjugate tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, and a Fabry Perot liquid crystal tunable filter.

17. The instrument of claim 13, further comprising an interferometer selected from the group consisting of a polarization-independent imaging interferometer, a Michelson interferometer, a Sagnac interferometer, a Twynam-Green interferometer, a Mach-Zehnder interferometer, and a tunable Fabry Perot interferometer.

* * * * *